United States Patent [19]

Woskow

[11] Patent Number: 4,830,005

[45] Date of Patent: May 16, 1989

[54] DISPOSABLE IN-PACKAGE LOAD TEST ELEMENT FOR PACEMAKERS

[75] Inventor: Robert M. Woskow, Los Angeles, Calif.

[73] Assignee: Siemens-Pacesetter, Inc., Sylmar, Calif.

[21] Appl. No.: 76,952

[22] Filed: Jul. 23, 1987

[51] Int. Cl.[4] ........................ A61N 1/00; H05G 00/00

[52] U.S. Cl. ............................................. 128/419 PT

[58] Field of Search .................. 128/419 PT, 419 PG, 128/419 P, 1 R; 206/328, 330, 331, 333

[56] References Cited

U.S. PATENT DOCUMENTS

| | | | |
|---|---|---|---|
| 3,508,538 | 4/1970 | Keller, Jr. | 128/419 PT |
| 3,625,201 | 12/1971 | Murphy | 128/419 PT |
| 3,798,542 | 3/1974 | Dempsey | 324/133 |
| 4,423,732 | 1/1984 | Tarjan et al. | 128/419 P |
| 4,476,869 | 10/1984 | Bihn | 128/419 PT |
| 4,605,007 | 8/1986 | Heraly | 128/419 PT |
| 4,705,042 | 11/1987 | Giurtino | 128/419 PT |

*Primary Examiner*—Francis Jaworski
*Assistant Examiner*—George Manuel
*Attorney, Agent, or Firm*—Bryant R. Gold; Leslie S. Miller; Henry M. Bissell

[57] ABSTRACT

A test device for use with a pacemaker to simulate the load of a heart. The device is designed for telemetering control and includes in its circuit a magnetic reed switch which opens and closes a load circuit in response to a remotely applied magnetic field. The device is intended to be disposable and is installed in circuit with the pacemaker terminals which normally connect to the heart leads. The device as thus installed is packaged in the sterile shipping package with the pacemaker and both permit the final checking of the pacemaker within its sterile pack prior to shipment and testing of the pacemaker in preparation for implantation without the necessity of opening the sterile package to conduct the test.

16 Claims, 2 Drawing Sheets

14 10 20 16 18 28 12

DISPOSABLE IN-PACKAGE LOAD TEST ELEMENT FOR PACEMAKERS

This invention relates to cardiac pacemakers and, more particularly, to an element to be included in a sterile packaged pacemaker to permit more thorough testing thereof prior to surgical implantation.

BACKGROUND OF THE INVENTION

It is common for the manufacturers of electrical equipment to test such equipment before packaging and shipping the equipment to distributors, sales outlets, end users and the like. Such testing may include checking the various modes of operation of the equipment for satisfactory performance, proper adjustment of controls within prescribed tolerances, operating ranges, etc. and it may also include several hours or days of operation ("burn-in") to check for stability and to detect possible premature failure. Still other tests may involve running the equipment under specified overload conditions, performing tests of certain components or portions of individual circuits within the equipment, and checking for weaknesses or the presence of defective components or other circuit parts which may not be readily apparent from test operation of the equipment. It is not uncommon for others down-line in the distribution channel leading to the ultimate end user to perform similar tests of the equipment before final disposition.

A cardiac pacemaker is a type of electrical equipment in which testing for proper, reliable operation is essential. Because of the nature of the use of a pacemaker, it is literally true that a life may be at stake if a pacemaker malfunctions during operation when implanted in a patient. For this reason, elaborate tests are performed during the manufacture of pacemakers to make them as reliable as possible.

A further, relatively unique demand is imposed on pacemakers by virtue of their ultimate use. The pacemaker and all of its internal components must be surgically sterile. Thus, after manufacture and testing, the pacemaker is sterilized and sealed in sterile packaging, to be maintained in sterile condition until the packaging is removed in preparation for implantation of the pacemaker by a surgical team.

An appreciation of the problem of testing an electronic component in a sterile package without invading the internal sterile environment of the component is evidenced in U.S. Pat. No. 4,605,007 of Heraly. That patent discloses an inner and outer container with feed-through contacts in the outer container to physically contact the electrical contacts of the sterilized electrical component. Thus circuit connections may be established with the outer contacts without affecting the sterile condition and environment of the inner contacts that constitute part of the electrical component in the sterile environment. This component, however, is only a part of a cardiac pacemaker and is not subject to the problems of testing the terminal connectors and lead circuitry of an overal pacemaker. The provision of access to an internal, prepackaged electrical component which is taught by Heraly is akin to that which is customarily provided for testing drycells that are commonly marketed in a bubble pack package. A pair of small holes in the bubble pack are provided next to the drycell terminals so that a pair of voltmeter electrodes can be applied to the terminals without opening the package. Heraly adapts that principle to protection of a sterile environment in which an electrical component is packaged.

It is generally possible to conduct certain tests of pacemakers while they are still enclosed within their sterile packaging. Modern pacemakers not only can receive programmed instructions, but they can also send back messages regarding the status of the pacemaker. This ability to remotely interrogate the pacemaker by wireless means is called telemetry. Telemetry can provide a readout of the various programmable functions of a pacemaker and an indication of the properties of certain of the pacemaker components. Final testing of a cardiac pacemaker is generally performed by the surgical team in preparation for implantation. It is common to have a plurality of pacemakers at hand, still in their sterile packaging, in the operating room at the time of final testing so that no time need be wasted in drawing another unit from inventory if a defect is discovered in the one under test.

Heretofore it has been difficult, if not impossible, to provide a final test of the terminal connectors for the leads which are to be inserted in the patient's heart and plugged into the pacemaker for implantation, yet these terminal connectors constitute one of the important potential failure points of a pacemaker. While certain types of terminal failures may be detected at final telemetry testing, others cannot. For example, an unusually low impedance in the terminal connector circuit may suggest a break in insulation. However, since the terminal circuit is open prior to connection to the heart leads, a break in a wire leading to the terminal does not provide any different indication and therefore cannot be detected until the leads are connected to the pacemaker. Detection of such a failure at this points represents a setback in the surgery time schedule, necessitating the susbsitution of another pacemaker which requires duplication of the programming, testing. etc. already conducted on the first pacemaker.

SUMMARY OF THE INVENTION

In brief, arrangements in accordance with the present invention comprise a prefabricated until which can be temporarily installed in a circuit connection to the pacemaker terminals and is adapted to sterilization and packaging with the pacemaker. Thus the unit circuitry can be used during the final testing of the pacemaker by the surgical team to permit tests of the pacemaker terminal connectors and circuits which were not heretofore possible without removing the pacemaker from its sterile packaging.

In its simplest embodiment, a unit in accordance with the present invention comprises a resistor in series with a normally open magnetic reed switch. This series circuit is placed electrically between the signal output and return terminals of the pacemaker. The circuit remains attached to the pacemaker in the sterile package. It presents no electrical load to the pacemaker circuits because the reed switch is in the normally open position. Usually a permanent magnet in the interrogation device is used to close a reed switch which is internal to the pacemaker. Thus the unit is effective in the testing of an associated pacemaker with any telemetry interrogation system that utilizes a magnetic field.

When the reed switch of the unit is closed by the application of a magnetic field, the electrical load comprising the unit's resistor (plus the negligible resistance of the reed switch) is placed across the pacemaker terminals. Although the value of the resistor is not critical, it preferably approximates the load that a heart presents to the pacemaker, typically 300 to 500 ohms. When such a load value is used for the resistor, the measured data telemetered back to the interrogating device will be representative of data measured from a properly implanted pacemaker. In addition, the pacemaker connector/feedthrough terminal integrity may be tested. Such a device thus further improves the reliability and thoroughness of the testing procedure which occurs prior to implantation. Since it has only two electrical components, the device is extremely reliable. Moreover, because of its simplicity and low number of parts, its cost is very low. The device is designed to be discarded after a single use.

Variations of the invention are designed for use with different kinds of pacemakers. The embodiment as just described is for use with a single chamber, bipolar (not inline) pacemaker).

In another embodiment of the present invention, two series circuit paths, each including a single resistor and magnetic reed switch, are provided for connection to the terminals of a unipolar, dual-chamber pacemaker. In this embodiment, the distal ends of the two individual paths are tied together and connected to a pacemaker return contact.

Still another embodiment of the present invention incorporates a pair of separate circuit paths, each including a load resistor and a magnetic reed switch, with both ends of these circuit paths being located for coupling to the terminal leads of a dual chamber, inline, bipolar pacemaker when the device is inserted into the female terminal configurations of the pacemaker.

The circuit components of each unit are sealed within a plastic body, from which only the electrical lead terminals extend. The plastic body is configured to mate with the female terminal configuration of the pacemaker with which it is associated and, for units providing a pacer return contact, the configuration of the plastic body is such that the return contact is fixed in a position and attitude to contact the metal case of the pacemaker when the unit is inserted into the female terminal connectors of the pacemaker.

BRIEF DESCRIPTION OF THE DRAWINGS

The above and other objects, features and advantages of the present invention will be more apparent from the following more particular description thereof presented in conjunction with the accompanying drawings, wherein.

DETAILED DESCRIPTION OF THE INVENTION

The following description is of the best presently contemplated mode of carrying out the invention. The description is not to be taken in a limiting sense but is made merely for the purpose of describing the general principles of the invention. The scope of the invention should be determined with reference to the attached claims.

Figure 1:
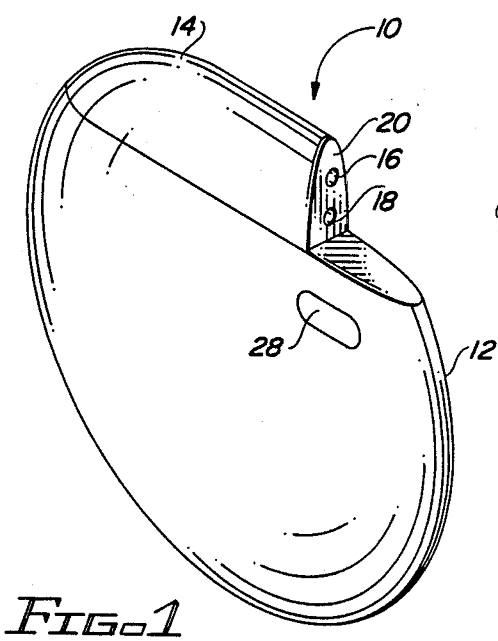
FIG. 1 is an enlarged view of a cardiac pacemaker to which the present invention is related.

Implantable cardiac pacemakers of the type here involved have a housing which is of more or less standard size and shape for those models of pacemakers which are presently being manufactured. A typical pacemaker 10 is shown in an enlarged view in FIG. 1. Such a pacemaker is approximately the size and weight of a conventional pocket watch. Typically the pacemaker 10 of FIG. 1 has a housing comprising a metal case 12 to which is affixed a connector top 14, usually formed of plastic. The pacemaker 10 is shown with a pair of openings 16, 18 in the end wall 20 of the connector top. These openings 16, 18 are the outer ends of bores which extend back into the connector top and are provided to receive the terminal connectors of leads which extend to the patient's heart. The pacemaker may be single chamber or dual chamber, unipolar or bipolar, inline or not inline, and a test element configuration in accordance with the present invention may be adapted accordingly to be usable with a given pacemaker.

Figure 2:
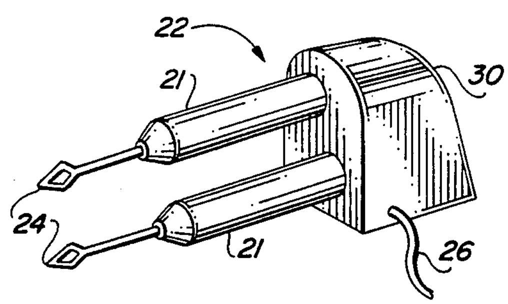
FIG. 2 is a perspective view of one particular arrangement in accordance with the present invention.
Figure 4:
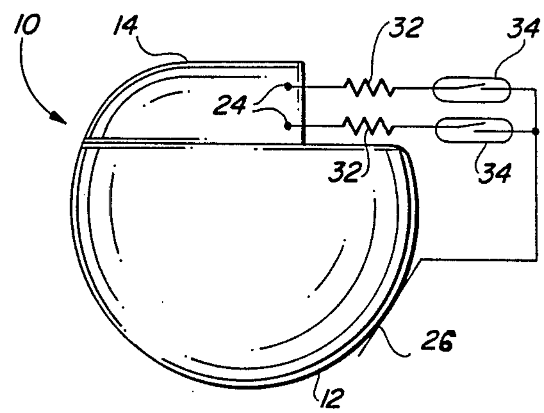
FIG. 4 is a schematic diagram representing circuitry of the present invention in association with a pacemaker like that shown in FIG. 1.

FIG. 2 shows a particular arrangement of the present invention configured for a dual chamber unipolar pacemaker and corresponds to the circuit arrangement depicted in FIG. 4. Device 22 is shown with two wire terminal connectors 24, one for each of two pacer outputs, and a pacer return contact 26 which makes contact with the pacemaker case in the region 28 (FIG. 1) when the unit 22 is mounted in place on the pacemaker 10. Device 22 has a pair of cylindrical hollow rods 21 extending longitudinally from a base portion 30. By means of this arrangement, the rods 21 and the terminal connectors 24 are maintained in the proper orientation to enter the bores 16, 18 of the pacemaker when the device 22 is installed. Each cylindrical rod contains a resistor 32 and a magnetically responsive reed switch 34, interconnected with the return contact 26 as shown in FIG. 4.

Figure 5:
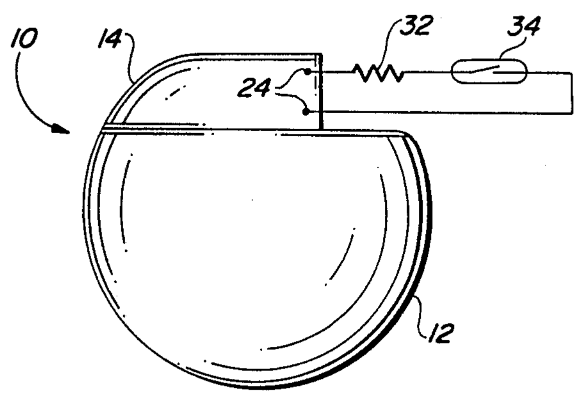
FIG. 5 is a schematic view showing circuitry of another arrangement in accordance with the present invention in association with a pacemaker like that represented in FIG. 1.

For the configuration represented in FIG. 5, which shows a single chamber, bipolar (not inline) pacemaker, wherein the return contact 26 is dispensed with, only one resistor and switch combination 32, 34 is present in one of the cylindrical rod portions 21. The other member 21 only contains a wire extending from the lower terminal connector 24 and completing the circuit to the reed switch 34.

Figure 3:
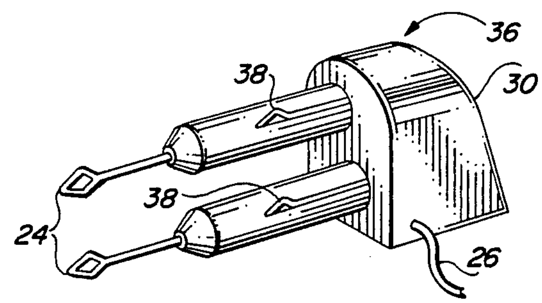
FIG. 3 is a perspective view of another particular arrangement in accordance with the present invention.
Figure 6:
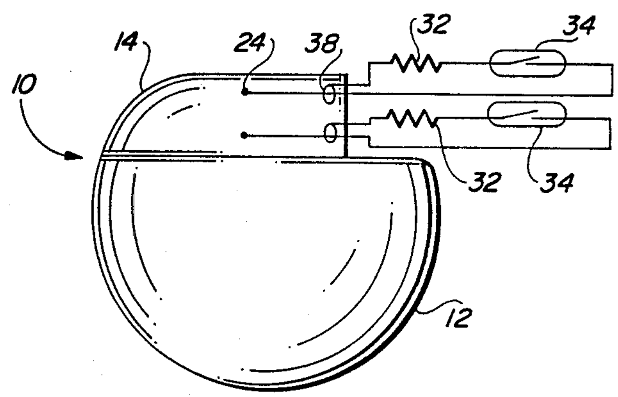
FIG. 6 is a schematic diagram representing circuitry of still another arrangement in accordance with the present invention in association with a pacemaker like that shown in FIG. 1.

FIG. 3 shows a test device 36, like the device 22 of FIG. 2 except that the device 36 is provided with added contact elements 38 for use with a dual chamber, inline, bipolar pacer, such as the combination represented schematically in FIG. 6. In this arrangement, the return contact 26 is not in the circuit; it is not used electrically but is included for uniformity of fabrication.

In the circuit of FIG. 5, one of the terminals 24 is the pacer output; the other is for the signal return. In the circuit of FIG. 6, the terminals 24 are typically pacer output leads while the connectors 38 correspond to the signal return contacts where they connect into the pacemaker 10.

Figure 7:
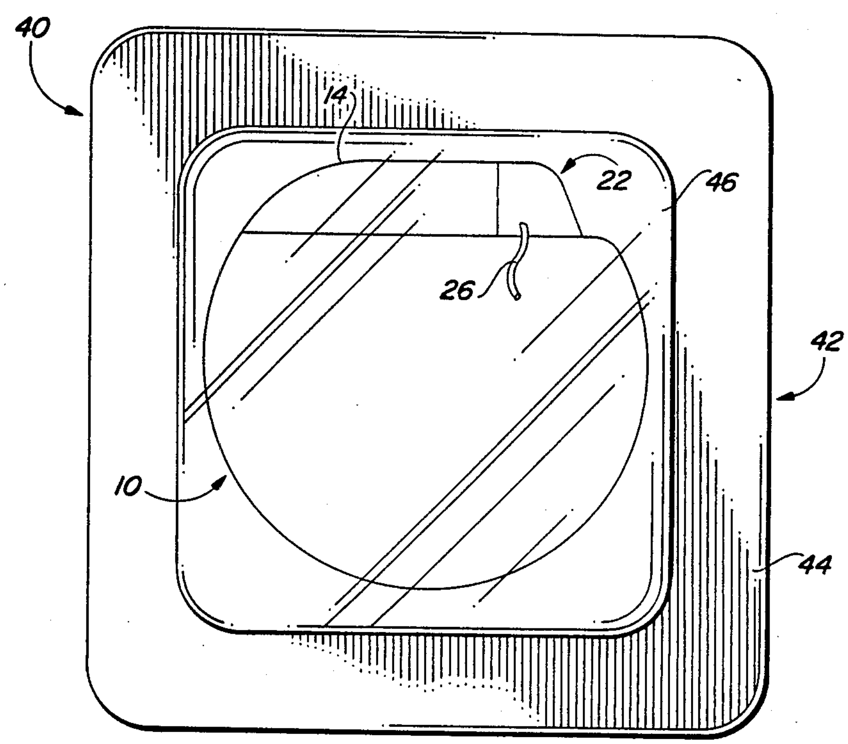
FIG. 7 is a side view of a pacemaker and a disposable device of the present invention as installed within a sterile package, ready for testing.

FIG. 7 shows a combination 40 of a pacemaker 10 as packaged within a sterile pack 42, ready for shipment or for testing in preparation for implantation. The in-package test device 22 is shown installed on the pacemaker with the terminal connectors inserted into the plastic cap 14. The pack 42 is shown with a peripheral sealing edge 44 which surrounds the trapped, sterile chamber 46 in which the pacemaker 10 is maintained in a sterile environment. The chamber 46 typically contains a sterilizing gas which serves to sterilize the pacemaker and its components and to maintain the contents of the chamber sterile as long as the integrity of the package is not disrupted. The material of the pack 42 is typically of transparent plastic so that the pacemaker is clearly visible within the package.

With devices in accordance with the present invention, faulty connector elements and feedthrough to internal electronics of a package pacer can be detected without opening the sterile package. This permits a final operational test of the pacemaker within its package before the unit is shipped. Telemetered interrogation of the packaged pacer occurs with the pacer under load—i.e., in circuit with the series resistor 32 of the test device—yet when the interrogation device is removed, the load is removed from the pacer circuitry upon the opening of the reed switch 34 so that there is no excessive battery drain between the time of manufacture and the time of implantation. At the other end of the pipeline, when the unit is prepared for implantation, the surgical implantation team can verify electrical functionality of the pacer by the same means before the sterile package is opened.

It will be understood that the order of the elements in the series circuit path, the reed switch and the resistor, may be reversed, just as the output and return terminals 24 of the single chamber bipolar pacer of FIG. 5 may be interchanged.

The concept of the present invention is independent of the pacer manufacturer or pacer design, and is readily adaptable to different terminal configurations. The only requirement is that a magnetic field must be present to activate the reed swich during telemetered interrogation. However, equivalent devices providing the capability of the reed switch may be substituted in the test device circuit(s). For example, a Hall effect switch or some other proximity switch which can open and close an electrical path in response to a remote signal or applied field may be used.

If desired, a light emitting diode (LED) or similar indicator may also be placed in the circuit, in series with the device as shown, thereby providing a simple, quick diagnostic tool which requires only the presence of a magnetic field to cause activation. Other variations in accordance with the present invention may be devised.

Although there have been described above specific arrangements of a disposable in-package load test element for pacemakers in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A test device for use in association with a pacemaker to test the integrity of pacemaker terminal circuitry and connectors to which heart leads may be coupled comprising:

an electrical component for simulating a heart load;

a switch element connected electrically in a first series circuit with said electrical component for selectively switching said component into and out of the terminal circuitry of the pacemaker, said switch element being capable of responding to a magnetic field, wherein said switch element responds to said magnetic field within a sterile pacemaker shipping package from a magnetic means located outside of said sterile pacemaker shipping package;

first and second contact elements connected in series with said first series circuit, said first and second contact elements adapted to mate with terminal circuitry of the pacemaker; and support means for mounting said first and second contact elements in a physical configuration to align with terminal circuit contacts of the pacemaker.

2. The device of claim 1 wherein the electrical component is a resistor having a value in a range to simulate a heart as a load on the pacemaker.

3. The device of claim 2 wherein said resistor value is in the range of 300 to 500 ohms.

4. The device of claim 1 further comprising a body including said support means, said support means comprising extended mounting portions of said body, said body encapsulating said electrical component and said switch element, said body and extended mounting portions being formed of plastic.

5. The device of claim 1 further including a third contact element, a second electrical component for simulating a heart load, and a second switch element connected in series with said second electrical component to form a second series circuit, said second series circuit being adapted to electrically connect to a pacer output terminal in series with said second contact element, said second series circuit having a common connection point with said first series circuit, said common connection point being directly connected to said third contact element adapted to contact the pacemaker case to simulate a pacemaker return contact.

6. In combination, a pacemaker, a test device installed in association with the pacemaker, and a package enclosing the pacemaker and test device in a sealed sterile environment, said device comprising:

an electrical component for simulating a heart load;

a switch element connected electrically in a first series circuit with said electrical component for selectively switching said component into and out of the terminal circuitry of the pacemaker, said switch element being remotely actuable;

a pair of contact elements connected in series with said component and said switch element for coupling said component and switch element in circuit with terminal circuitry of the pacemaker; and support means mounting said contact elements in a physical configuration to mate with terminal circuit contacts of the pacemaker.

7. The device of claim 6 wherein the electrical component is a resistor having a value in a range to simulate a heart as a load on the pacemaker.

8. The device of claim 8 wherein said resistor value is in the range of 300 to 500 ohms.

9. The device of claim 6 wherein said switch element is capable of responding to a magnetic field within a sterile pacemaker shipping package from magnetic field generating means located outside of said sterile pacemaker shipping package.

10. The device of claim 9 wherein said switch element is a magnetic reed switch.

11. The device of claim 6 further comprising a body including said support means, said support means comprising extended mounting portions of said body, said body encapsulating said electrical component and said switch element, said body and extended mounting portions being formed of plastic.

12. The device of claim 1 further comprising a light emitting diode, wherein said diode is utilized for providing a visible indicator of the integrity of the terminal circuitry of the pacemaker.

13. The device of claim 1 wherein said switch element is a magnetically sensitive Hall effect semiconductor switch.

14. The device of claim 1 wherein said switch element is a magnetically actuable reed switch.

15. A test device for use in association with a pacemaker having a pacer output terminal and a pacer return terminal to which heart leads may be coupled, said test device comprising:

first and second series circuits each including a resistor and a magnetic reed switch;

first and second contact element, said first contact element connected in series with said first series circuit, said second contact element connected in series with said second series circuit, said first and second contact elements adapted to electrically mate to said pacer output terminal;

third and fourth elements, said third contact element connected in series with said first series circuit, said fourth contact element connected in series with said second series circuit, said third and fourth contact elements adapted to electrically mate to said pacer return terminal to simulate a pacemaker return contact; and support means for mounting said first, second, third, and fourth contact elements in a physical configuration to align with said pacer output and pacer return terminals of the pacemaker, whereby said test device may be used to test the integrity of said pacer output terminal and said pacer return terminal.

16. The device of claim 14 further comprising a body encapsulating said first and second series circuits, said support means extending from said body and said support means being formed of plastic.

* * * * *